United States Patent
Agrawal et al.

(10) Patent No.: US 8,551,780 B2
(45) Date of Patent: Oct. 8, 2013

(54) ELECTROPORATION BUFFER COMPOSITION AND METHOD OF USE

(75) Inventors: Deepak Kumar Agrawal, Tampa, FL (US); Warren Jackson Pledger, Odessa, FL (US); Jonathan A. Kluft, Tampa, FL (US); Asha Agrawal, Tampa, FL (US)

(73) Assignees: H. Lee Moffitt Cancer Center & Research Institute, Inc., Tampa, FL (US); University of South Florida, Tampa, FL (US); Proteacel, LLC, Tampa, FL (US)

( * ) Notice: Subject to any disclaimer, the term of this patent is extended or adjusted under 35 U.S.C. 154(b) by 554 days.

(21) Appl. No.: 12/364,409

(22) Filed: Feb. 2, 2009

(65) Prior Publication Data

US 2009/0197335 A1 Aug. 6, 2009

Related U.S. Application Data

(60) Provisional application No. 61/063,189, filed on Feb. 1, 2008.

(51) Int. Cl.
*C07K 14/435* (2006.01)

(52) U.S. Cl.
USPC ........... 435/375; 435/461; 435/404; 435/450; 530/363

(58) Field of Classification Search
None
See application file for complete search history.

(56) References Cited

U.S. PATENT DOCUMENTS

| | | | | |
|---|---|---|---|---|
| 5,281,522 A * | 1/1994 | Senyei et al. | ................... | 435/7.9 |
| 5,763,203 A * | 6/1998 | Ugelstad et al. | ............. | 435/7.24 |
| 6,511,815 B1 * | 1/2003 | Burke et al. | ................... | 435/7.8 |
| 7,094,789 B2 * | 8/2006 | Yamada et al. | ............... | 514/307 |

\* cited by examiner

*Primary Examiner* — Jim Ketter
(74) *Attorney, Agent, or Firm* — Saliwanchik, Lloyd & Eisenschenk (57) ABSTRACT

The subject invention concerns an electroporation buffer that allows for enhanced transfection efficiency and cell viability of cells during application of an electric current. Buffers of the invention provide for maximum transfer of target particles into cells while maintaining the health and growth potential of the cell population. Compositions of the invention comprise electroporation buffers of approximately physiological ionic strength and pH, and having serum or purified proteins, such as serum albumin, added thereto. The subject invention is suitable for use with any cell type. The subject invention also concerns methods of electroporation using an electroporation buffer of the invention.

22 Claims, 6 Drawing Sheets

ELECTROPORATION BUFFER COMPOSITION AND METHOD OF USE

This application claims the benefit of U.S. Provisional Application No. 61/063,189, filed Feb. 1, 2008, and titled "Materials and Methods for Optimal DNA Transfer to Living Cells by Electroporation", the entire disclosure of which is hereby incorporated by reference in its entirety.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

This invention was made with Government support under Grant No. R01 CA089301 awarded by the National Institutes of Health. The Government has certain rights in this invention.

FIELD OF THE INVENTION

The present invention relates to systems and methods for improved transfer of DNA into living cells by electroporation and, more particularly, to improved electroporation buffers that increase cell viability.

BACKGROUND OF THE INVENTION

Transfection is the process of introducing foreign particles such as nucleic acids (DNA, RNA, etc.) and proteins into the cell. Two fundamental goals of transfection are: i) to introduce the desired amount of target foreign particle(s) into the cells, thereby maximizing transfection efficiency, and ii) to preserve the health and life of the cells to the greatest extent, hence maximizing cell viability.

The general method of transfection is as follows: 1) Culture cells to desired cell density; 2) Transfect cells with method of choice, commonly calcium complexes, liposome complexes, or electroporation; and 3) Analyze transfected cells. Several common methods of transfection include liposome-mediated transfection, microinjection, calcium phosphate-based transfection, and electroporation.

Liposome-mediated transfection involves the enclosure of a nucleic acid within a lipid-based vesicle, which, as a nonpolar complex, facilitates its movement across the cell membrane and into the cell. Lipid-mediated transfection is widely used but, with many cell lines, it suffers from a low rate of transfer of foreign material into the cell. The lipid vesicles, or liposomes, are also toxic to cells at higher concentrations.

Microinjection is the use of a micro-needle to inject foreign material directly into the cell. It is a time-inefficient method of transfection when working with even moderately sized cell numbers.

Calcium phosphate-based methods involve the formation of a complex between DNA and calcium phosphate, which is then taken in by the cell. This method does not allow for an efficient uptake of foreign material across a wide variety of cell lines.

Electroporation involves the application of an electrical current to a mixture of cells so as to cause the opening of the cell membrane and subsequent entry of material into the cell through pores. Although it tends to allow for higher transfection efficiency than many other methods, electroporation can also be very harmful to the cell. Depending on the nature of the buffer as well as the degree and length of the electric shock, electroporation can cause the loss of greater than 90% of the starting population of cells.

Finding a buffer in which to electroporate cells without compromising cell viability is critical to the process of performing a transfection experiment. The following are commonly used electroporation buffers:

a) Buffers containing basic media or basic media supplemented with 10% serum. Although very commonly used, they tend to be of poor quality as electroporation buffers. They cause drastically diminished cell viability and low transfection efficiency.

b) Hypoosmolar buffers. These buffers are used on the premise that they cause the uptake of water into the cell prior to electroporation, thereby increasing cell volume and pore formation, which leads to improved transfection efficiency. Although modest gains in transfection efficiency and cell viability are achieved, there is a risk that the low osmolarity of the buffer will cause cell lysing, reducing cell viability.

c) Buffers of low ionic strength. Because of their diminished conductivity, these buffers impose less electrical stress on the cell due to reduced current flow in the solution. This is thought to minimize electrically-induced damage to the cells being transfected.

d) Buffers supplemented with DEAE-dextran. It is hypothesized that these buffers allow nucleic acids to associate loosely with the cell membrane, decreasing the distance the foreign particle has to travel to enter the cell, and allowing for higher transfer of material.

The general disadvantages of the above described electroporation buffers include:

a) a failure to allow for high transfer of foreign material into the cell;
b) high cytotoxicity;
c) inconsistent performance with respect to transfer efficiency and/or cytotoxicity;
d) inability to be used with little modification across a wide variety of cell lines;
e) complex or time-consuming protocols.

Thus, there remains a need in the art for electroporation buffers that provide for improved cell viability and increased transfection efficiency.

SUMMARY OF THE INVENTION

The subject invention concerns compositions and methods for electroporation that provide for high cell viability and high transfer of foreign material into a cell. The invention provides for improved electroporation across a wide variety of cell lines. Electroporation buffers of the invention serve to stabilize the cells and prevent cell death as a result of electrical stress. Compositions of the invention comprise electroporation buffers of approximately physiological ionic strength and pH, and having serum or purified proteins, such as serum albumin, added thereto.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

The subject invention concerns compositions and methods for electroporation that provide for high cell viability and high transfer of foreign material into a cell. The invention provides for improved electroporation across a wide variety of cell lines. Electroporation buffers of the invention serve to stabilize the cells and prevent cell death as a result of electrical stress.

As used in this specification, the singular forms "a", "an", and "the" include plural reference unless the context clearly dictates otherwise. Thus, for example, a reference to "a cell" includes more than one such cell. Reference to "a polynucleotide" includes more than one such polynucleotide. Reference to "a polypeptide" or "agent" includes more than one such polypeptide or agent, and the like.

The terms "transfection", "transformation", and "introduction", and grammatical variations thereof, are used interchangeably herein to refer to the insertion of an exogenous molecule (e.g., a nucleic acid sequence encoding a peptide or protein, or fragment, homolog, or variant thereof), into a host cell, irrespective of the method used for the insertion, the molecular form of the molecule that is inserted, or the nature of the cell (e.g., prokaryotic or eukaryotic).

In one embodiment, a composition of the invention comprises an electroporation buffer of approximately physiological ionic strength and pH, and serum or purified proteins. The pH of the buffer can be manipulated using any common buffering agent, including but not limited to HEPES, Tris, or a combination of sodium phosphate compounds. Ionic strength of an electroporation buffer of the invention can be manipulated using salts such as sodium chloride, potassium chloride, and other salts compatible with cell growth and physiological conditions.

Electroporation buffers of the invention comprise serum at a final concentration of at least about 30% (v/v). In one embodiment, the final serum concentration can range from about 30% to about 90%. In another embodiment, the final serum concentration can range from about 40% to about 80%. In one embodiment, a composition of the invention comprises an electroporation buffer comprising one or more purified proteins at concentrations above about 2% (w/v). In one embodiment, the buffer comprises purified protein at concentrations at or above about 3% to about 5% (w/v) or greater. In a specific embodiment, the purified protein is a serum albumin or a globulin. The serum or purified proteins can be from any mammalian species including human, primate, bovine, murine, canine, feline, porcine, caprine, equine, and ovine. In another embodiment, the serum or purified proteins are from a fish or an avian species.

An electroporation buffer of the invention, in addition to comprising serum or a purified protein, such as serum albumin, can also comprise one or more osmolytes. In one embodiment, an electroporation buffer of the invention comprises an osmolyte that is a carbon polyol. Carbon polyols are alcohols containing multiple hydroxyl groups. In one embodiment, the carbon polyol is a 5 or 6 carbon polyol. In a specific embodiment, the carbon polyol is one or more of xylitol, sorbitol, arabitol, maltitol, glycerol, erythritol, mannitol, isomalt, and lactitol. In one embodiment, a carbon polyol is present in the electroporation buffer at a final concentration of about 1 mM to about 500mM. In a further embodiment, a carbon polyol is present in the electroporation buffer at a final concentration of about 5 mM to about 500 mM. In a specific embodiment, a carbon polyol is present in the buffer at a final concentration of about 250 mM. In an exemplified embodiment, the carbon polyol is xylitol present in a final concentration of about 50 mM.

The subject invention also concerns methods of using an electroporation buffer of the invention. In one embodiment, a method of the invention comprises providing cells in an electroporation buffer of the invention; contacting the cells with a target molecule to incorporate into the cells; and subjecting the cells to an electrical current sufficient to transfect the target molecule into a cell. In one embodiment, the target molecule is a nucleic acid or protein or a combination of both. In a specific embodiment, the nucleic acid is DNA (e.g., cDNA, genomic DNA, synthetic DNA, etc.) or RNA (e.g., mRNA, miRNA, rRNA, snRNA, shRNA, siRNA, etc.). The methods can be practiced using standard electroporation protocols and any suitable electroporation devices, such as those manufactured by BioRad (e.g., Gene Pulser MXcell System) and Sonidel, Ltd.

In one embodiment, a composition of the invention comprises a buffer that (i) closely mimics intracellular pH using any common buffering agent, including HEPES, Tris, or a combination of sodium phosphate compounds, (ii) contains salt in the form of sodium chloride, potassium chloride, or any other salt compatible with cell growth, and (iii) serum supplemented to a final concentration range of 30-90% (volume/volume), or between 40-80%, and (iv) a 5 or 6 carbon polyol, such as xylitol, arabitol, or sorbitol, in the concentration range of 5 mM-500 mM, and preferably 250 mM.

The subject invention also concerns kits comprising in one or more containers reagents for practicing the present invention. In one embodiment, a kit can comprise an electroporation buffer of physiological ionic strength and pH, and a serum or purified protein pre-mixed in the buffer or provided separately from the buffer for addition thereto. The serum provided can be sufficient for a final concentration in the buffer of any concentration from about 30% to about 95% (v/v). A kit of the invention can also optionally include one or more osmolytes. In one embodiment, the osmolyte is a carbon polyol. In a specific embodiment, the osmolyte is a 5 or 6 carbon polyol. In a more specific embodiment, the carbon polyol is xylitol, sorbitol, arabitol, maltitol, glycerol, erythritol, mannitol, isomalt, or lactitol. The kit can also optionally include agents for adjusting ionic strength and pH of the buffer, such as HEPES, Tris, sodium phosphate compounds, sodium salts, potassium salts, etc. In another embodiment, a kit of the invention can include one or more purified proteins for addition to the electroporation buffer. The purified protein(s) provided can be sufficient for a final concentration of the protein in the buffer of any concentration from about 2% to about 5% (w/v) or greater.

The cell used with the compositions and methods of the invention can be prokaryotic or eukaryotic. In one embodiment, the cell is a bacterial cell. In another embodiment, the cell is a yeast, plant, or animal cell, e.g., an insect or a mammalian cell.

Following are examples that illustrate procedures for practicing the invention. These examples should not be construed as limiting. All percentages are by weight and all solvent mixture proportions are by volume unless otherwise noted.

Example 1

A detailed protocol for using an electroporation buffer of the present invention is given below.
1) U2OS cells, growing exponentially, were cultured in McCoy's media supplemented with 10% FBS at 37° C. in 100 mm plates to 60-90% density. The choice of culture medium is dictated by the cell type. This protocol is compatible with all known types of mammalian culture media.
2) Cells were detached from the plate by exposure to a 0.25% trypsin-EDTA solution.
3) Cells ($1 \times 10^5$ to $1 \times 10^7$) were collected in media from step 1 and pelleted at 200-1000g for 5 minutes.
4) This supernatant was removed, and the pelleted cells were resuspended in 400 µl electroporation buffer containing 50% bovine serum, 50 mM xylitol and containing buffering and salt agents from Dulbecco's modified Eagle medium (DMEM). DNA (1-5 µg) pGL 4.73 luciferase reporter construct (Promega) and 1-5 µg pZsGreen plasmid (Clontech) encoding a green fluorescent protein.
5) Cells were electroporated (BioRad gene Pulser II, 25 uF) at 4000V/cm in electroporation cuvettes.
6) Luciferase activity was taken at 24 hours post-transfection to provide a quantitative measure of transfection efficiency and cell viability, while fluorescent protein production was measured on a suitable microscope.

Figure 1:
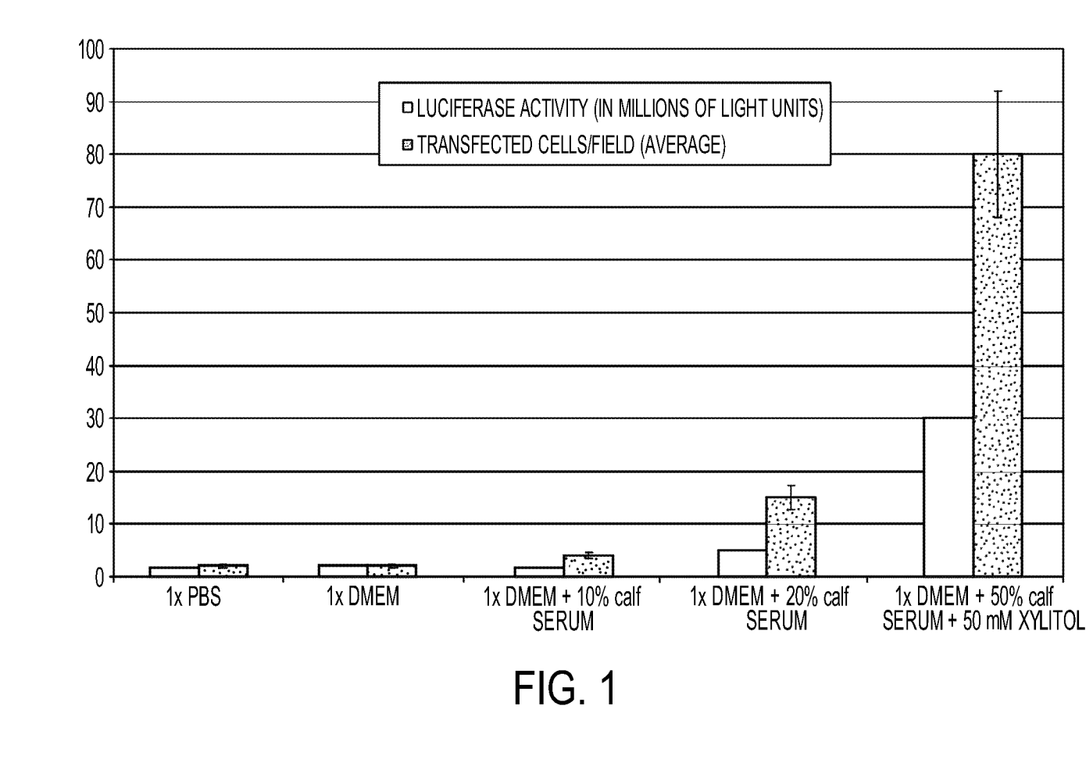
FIG. 1 shows transfection efficiency obtained with various buffers in U2OS cells.

FIG. 1 shows transfection efficiency obtained with various buffers in U2OS cells. U2OS cultures transfected with the indicated buffers were analyzed 24 hours after transfection, first by microscopy to determine the number of cells successfully transfected (filled-in bars), then harvested and assayed for luciferase activity (open bars). As is evident from FIG. 1, high values for transfection efficiency and cell viability are seen when the concentration of serum in the electroporation buffer is 50%. Decreased luciferase values are indicative of substantial loss of cell viability, which can be seen in FIG. 2. The methods of cell culture, harvesting, and measurement of luciferase activity were based on standard laboratory practices.

Example 2

Figure 2:
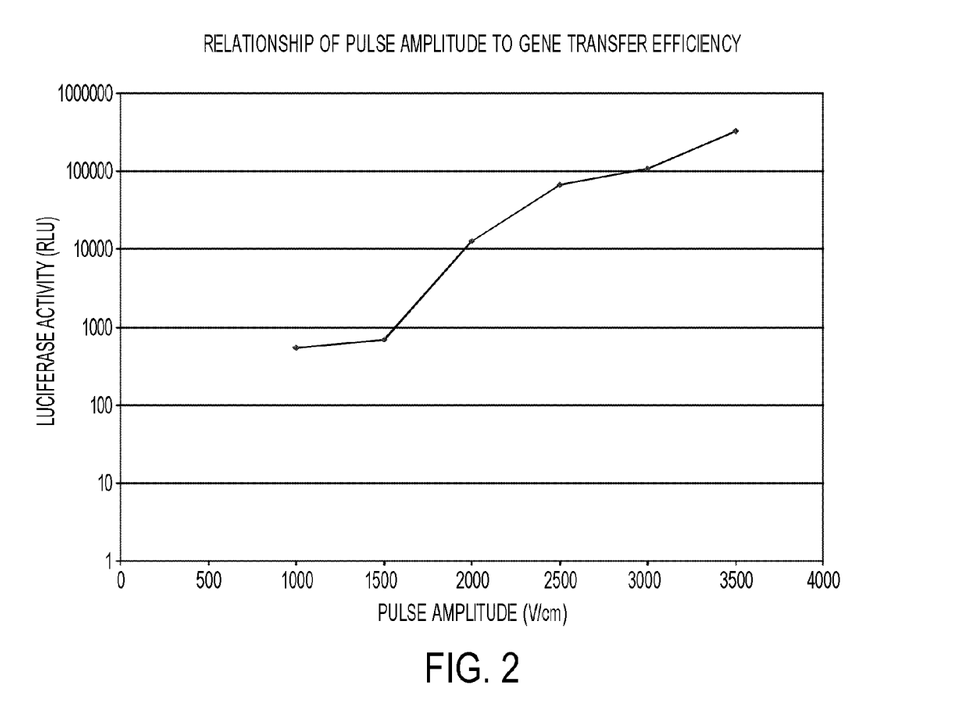
FIG. 2 shows the relationship of pulse amplitude to the efficiency of DNA transfer in a culture of an osteosarcoma cell line.

To determine the relationship of pulse amplitude to the efficiency of DNA transfer, a culture of an osteosarcoma cell line, MG63, was harvested for electroporation by standard tissue culture methods and concentrated by centrifugation (3 minutes at 200×g). The pelleted cells were resuspended in electroporation medium comprised of growth medium (DMEM) containing 50% bovine serum and 50 mM xylitol. Plasmid DNA (pGL4.73) encoding the gene for luciferase was added to the resuspended cells and the mixture was subjected to electroporation (Biorad GenePulser II, 25 uF capacitance) at voltages ranging from 1000 V/cm to 3500V/cm. Electroporated cells were collected and diluted in growth medium, plated in a tissue culture dish for 24 hours. After this incubation, luciferase activity was measured to determine DNA transfer efficiency. The resulting data is shown in FIG. 2.

Example 3

Figure 3:
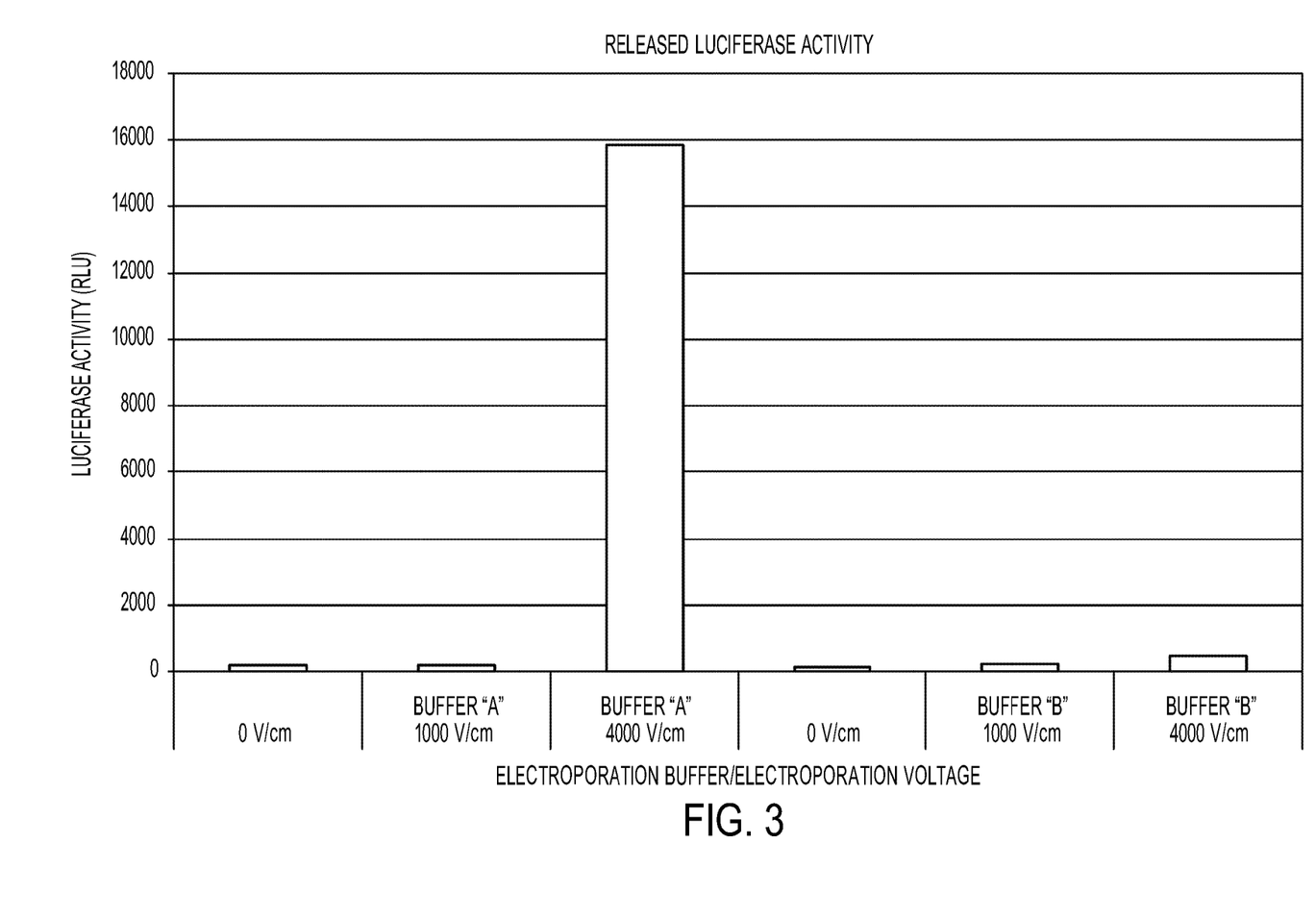
FIG. 3 shows how the omission of physiological salt in the buffer causes extremely high levels of cell lysis at high voltages required for efficient electroporation in difficult to transfect cell lines.

To determine the salt requirement for achieving protection in buffers containing high concentrations of serum, we compared the extent of cell lysis at high sucrose, low salt conditions and no sucrose, isotonic salt described in this application. Buffer "A" was prepared with 10 mM phosphate, 250 mM sucrose, 1 mM MgCl2, pH 7.2, conductivity of 1400 uS and mixed with bovine serum to give a final concentration of 50% serum. Buffer "B" made in accordance with the principles in this application (10 mM HEPES, 160 mM NaCl, 50 mM xylitol, 50% bovine serum). MG63 cells stably expressing luciferase were prepared as described above and resuspended in either Buffer "A" or Buffer "B", subjected to electroporation at either 1000 V/cm or 4000 V/cm, diluted 1:5 in growth medium, and incubated at 37° C. for 3 hours. At the end of the incubation, cell lysis was determined by removal of the cells by centrifugation and performing luciferase assays on the supernatant. Luciferase is an intracellular enzyme, and thus any enzyme appearing in the supernatant was the result of cell lysis from electroporation. The data are shown in FIG. 3, from which it is clear that the omission of physiological salt in the buffer causes extremely high levels of cell lysis at high voltages required for efficient electroporation in difficult to transfect cell lines.

Example 4

Figure 4A:
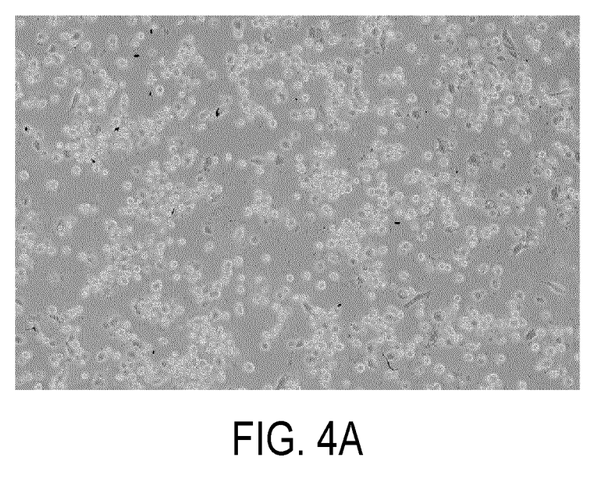
FIGS. 4A-4B show efficient delivery of pZsGreen to dendritic population without loss of maturation ability evidenced by the formation of "veils" on the transfected cells.
Figure 4B:
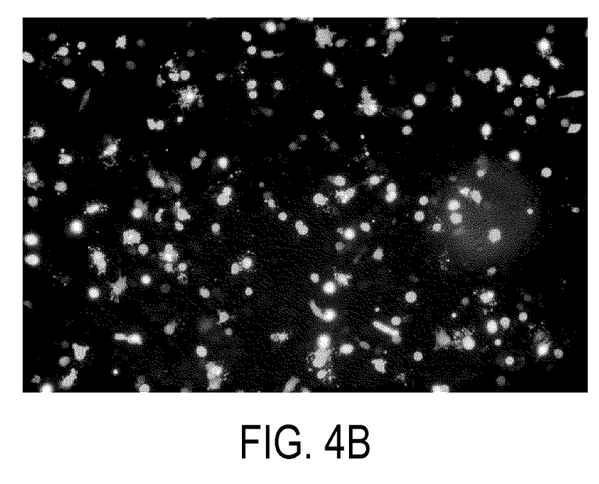

To test the current formulation for its ability to deliver DNA into "difficult to transfect" cells, an experiment was performed with human dendritic cells. These cells, prepared using standard culture medium for dendritic cells. Cultured cells were collected and concentrated by centrifugation, resuspended in electroporation buffer (RPMI containing 50% serum and 50 mM xylitol) containing 5 ug pZsGreen (Clontech), and subjected to electroporation at 4000V/cm (BioRad GenePulser II). After electroporation, cells were returned to culture medium as described above and incubated at 37° C. in 3.5 cm tissue culture dishes. Phase and fluorescence microscopy at 24 hours revealed efficient delivery of pZsGreen to the dendritic population without loss of maturation ability, as evidenced by the formation of characteristic "veils" on the transfected cells (FIG. 4).

Example 5

Figure 5A:
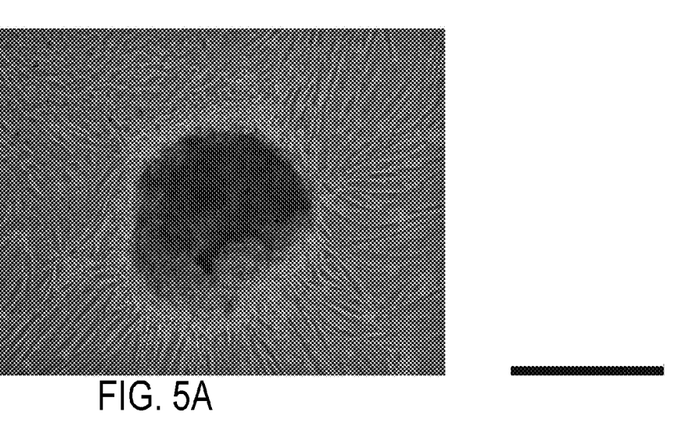
FIGS. 5A-B show that at 48 hours, pZsGreen was delivered homogeneously to stem cell contained in H9 colonies.
Figure 5B:
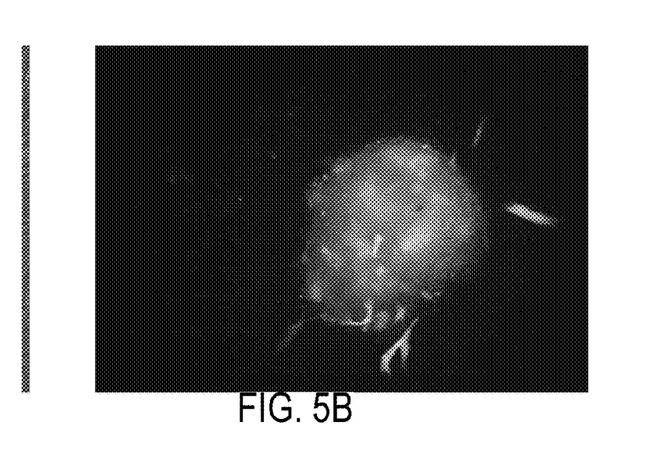

Human embryonic stem cells (hESC) have been found resistant to electroporation in many studies. We tested the ability of the current formulation to support DNA delivery to hESC H9 cells. H 9 cells were harvested using standard culture techniques for hESC cells. Briefly, H9 colonies grown on HFF feeder layers were manually dissected and the resulting pieces were aspirated into a 200 ul pipet tip, and transferred to a centrifuge tube. Once this procedure has been completed for approximately 25 colonies, the mixture was centrifuges as above to collect the cells, which were resuspended in 100 ul of electroporation buffer (1×MCDB-151 medium containing 50% bovine serum and 25 mM xylitol). Five micrograms of pZsGreen was added to this mixture, and the suspension was transferred to a 0.2 mm electroporation cuvette and subjected to electroporation at 4000 V/cm. The cells were plated onto HFF feeder cells and allowed to grow for 48 hours. Phase contrast and fluorescence microscopy at 48 hours of stem cell cultures (FIG. 5) revealed that pZsGreen was delivered homogeneously to cells contained in the H9 colonies.

Example 6

Human adult mesenchymal stem cells (MSC) have been found to be useful in generating a wide variety of cell types and have shown great potential for therapeutic applications. Currently, genetic modification of MSC is accomplished by using viral vectors, and it would be of significant interest if these cells could be manipulated by delivery of naked DNA. To test the ability of the current formulation to deliver DNA into MSC, we performed an experiment similar to that described in Example 5. MSC cultures were harvested using standard culture methods, collected by centrifugation and resuspended in electroporation buffer (1×MCDB-151 medium containing 50% bovine serum and 25 mM xylitol). Five micrograms of pZsGreen was added to this mixture, and the suspension was transferred to a 0.2 mm electroporation cuvette and subjected to electroporation at 4000 V/cm.

Figure 6A:
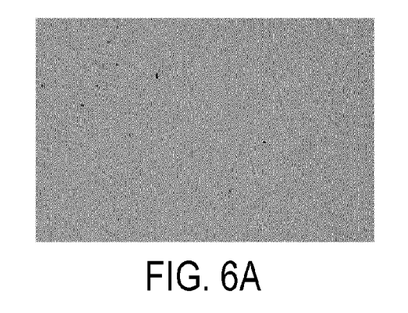
FIGS. 6A-6E show Phase contrast (A-C) and fluorescence microscopy (D-E) that reveals that pZsGreen is expressed in approximately 80% of the cells treated with the method described in this application.
Figure 6B:
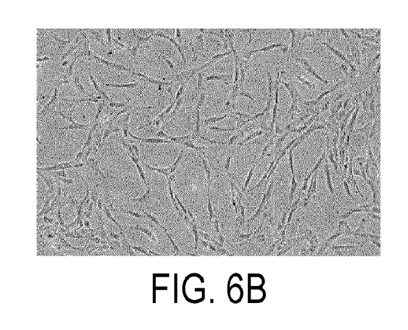
Figure 6C:
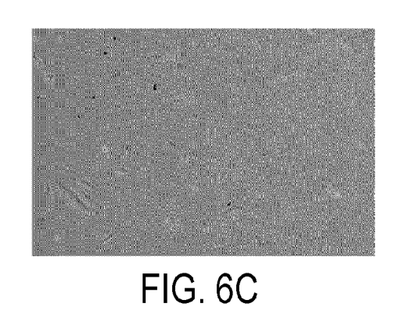
Figure 6D:
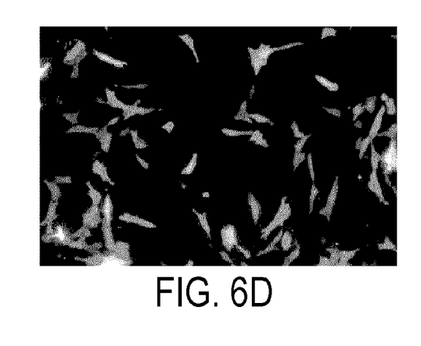
Figure 6E:
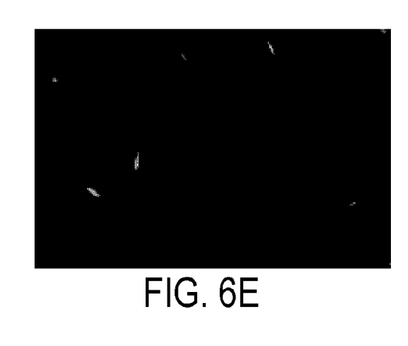

A second sample was processed in parallel with a commercial kit (manufactured by Amaxa GMBH, kit "A") designed for electroporation of MSC. The kit contained an MSC specific electroporation buffer, a 0.2 mm cuvette, and a pipet to transfer cells after electroporation. The kit was utilized exactly as outlined by the manufacturer. The electroporated cells in each case were transferred to growth medium (DMEM containing 10% fetal bovine serum) and incubated at 37° C. for 24 hours. Phase contrast of untreated (FIG. 6A) or electroporated cells (FIG. 6, B-C) and fluorescence microscopy (FIG. 6, D-E) revealed that pZsGreen was expressed in approximately 80% of the cells that had been treated with the method described in this application (Panel B and D), while less than 50% of the cells from the kit "A" experiment exhibited successful gene transfer (Panel C and E). Moreover, a comparison of the total cell yield by phase microscopy revealed that greater than 70% of the cells treated with the kit "A" regimen had been lost, while the cell yield for the method of the current application yielded little loss of cell viability.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. An electroporation buffer solution, comprising: at least one buffering agent, in such quantity that the pH of the solution is approximately physiological; at least one salt, in such quantity that the ionic strength of the solution is approximately physiological; serum, at a final concentration of about 30% to 90%, or a purified protein, wherein the purified protein comprises albumin or globulin, of about 2% to 5% (w/v) or greater; and a carbon polyol at 1 mM to about 50 mM.

2. The electroporation buffer solution of claim 1, wherein the electroporation buffer solution comprises the serum, and wherein the serum is at a concentration of approximately 40% to 60%.

3. The electroporation buffer solution of claim 2, wherein the carbon polyol is a 5 or 6 carbon polyol.

4. The electroporation buffer solution of claim 3, wherein the carbon polyol is one or more selected from among: xylitol, sorbitol, arabitol, maltitol, glycerol, erythritol, mannitol, isomalt, and lactitol.

5. The electroporation buffer solution of claim 4, wherein the carbon polyol is at a concentration of about 1 mM to about 25 mM.

6. The electroporation buffer solution of claim 1, wherein the electroporation buffer solution comprises the albumin of about 2% to 5% (w/v).

7. The electroporation buffer solution of claim 1, wherein the electroporation buffer solution comprises the globulin of about 2% to 5% (w/v).

8. A method of transfecting a cell with at least one target molecule, the method comprising the steps: providing the cell in an electroporation buffer solution; contacting the cell with the at least one target molecule; and applying an electrical current to the cell sufficient to transfect the target molecule into the cell,
wherein the electroporation buffer is comprised of: at least one buffering agent, in such quantity that the pH of the solution is approximately physiological; at least one salt, in such quantity that the ionic strength of the solution is approximately physiological; a serum of about 30% to 90% (v/v), or a purified protein, wherein the purified protein comprises albumin or globulin, of about 2% to 5% (w/v) or greater; and a carbon polyol at a concentration of 1 mM to about 50 mM.

9. A kit for an electroporation buffer solution, comprising:
(a) at least one buffering agent, in such quantity that the pH of the solution is approximately physiological;
(b) at least one salt, in such quantity that the ionic strength of the solution is approximately physiological;
(c) serum, at a final concentration of about 30% to 90% (v/v), or a purified protein at a concentration of about 30% to 90% (v/v), wherein the purified protein comprises albumin or globulin in an amount sufficient for a final concentration in the electroporation buffer solution of about 2% to 5% (w/v); and
(d) a carbon polyol at a concentration of 1 mM to about 50 mM.

10. The kit of claim 9, wherein the serum is at a concentration of approximately 40% to 60% (v/v).

11. The kit of claim 9, wherein the carbon polyol is one or more selected from among: xylitol, sorbitol, arabitol, maltitol, glycerol, erythritol, mannitol, isomalt, and lactitol.

12. The kit of claim 11, wherein the carbon polyol is at a final concentration of about 1 mM to about 25 mM.

13. The kit of claim 9, wherein the kit comprises the albumin of about 2% to 5% (w/v).

14. The kit of claim 9, wherein the kit comprises the globulin of about 2% to 5% (w/v).

15. The kit of claim 9, wherein the serum or purified protein of (c) and the buffering agent of (a) are in the same container.

16. The kit of claim 9, wherein the serum or purified protein of (c) and the buffering agent of (a) are in separate containers.

17. The electroporation buffer solution of claim 1, wherein the carbon polyol is at a concentration of 1 mM to 50 mM.

18. The electroporation buffer solution of claim 1, wherein the carbon polyol is at a concentration of 50 mM.

19. The electroporation buffer solution of claim 1, wherein the carbon polyol is at a concentration of 1 mM to 25 mM.

20. The electroporation buffer solution of claim 1, wherein the carbon polyol is at a concentration of 25 mM.

21. The electroporation buffer solution of claim 1, wherein the carbon polyol comprises xylitol.

22. The electroporation buffer solution of claim 1, wherein the carbon polyol comprises xylitol at a concentration of 50 mM.

* * * * *

UNITED STATES PATENT AND TRADEMARK OFFICE
CERTIFICATE OF CORRECTION

PATENT NO.         : 8,551,780 B2
APPLICATION NO.    : 12/364409
DATED              : October 8, 2013
INVENTOR(S)        : Deepak Kumar Agrawal et al.

It is certified that error appears in the above-identified patent and that said Letters Patent is hereby corrected as shown below:

In the Specification:

Column 1,
Lines 9-18, "This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

This invention was made with Government support under Grant No. R01 CA089301 awarded by the National Institutes of Health. The Government has certain rights in this invention."

should read

--This invention was made with Government support under Grant No. R01 CA089301 awarded by the National Institutes of Health. The Government has certain rights in this invention.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.--

Signed and Sealed this
Eleventh Day of February, 2014

Michelle K. Lee
*Deputy Director of the United States Patent and Trademark Office*